(12) United States Patent
Kramer et al.

(10) Patent No.: US 9,167,810 B2
(45) Date of Patent: Oct. 27, 2015

(54) COMPOUNDS DERIVED FROM HERBICIDAL CARBOXYLIC ACIDS AND TETRAALKYLAMMONIUM OR (ARYLALKYL) TRIALKYLAMMONIUM HYDROXIDES

(75) Inventors: Vincent J. Kramer, Westfield, IN (US);
David G. Ouse, Indianapolis, IN (US);
Norman R. Pearson, Carmel, IN (US);
Holger Tank, Zionsville, IN (US); Mark W. Zettler, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 1389 days.

(21) Appl. No.: 12/072,403

(22) Filed: Feb. 26, 2008

(65) Prior Publication Data
US 2008/0207453 A1 Aug. 28, 2008

Related U.S. Application Data

(60) Provisional application No. 60/903,417, filed on Feb. 26, 2007.

(51) Int. Cl.
*A01N 43/40* (2006.01)
*A01N 25/00* (2006.01)
*A01N 33/12* (2006.01)

(52) U.S. Cl.
CPC .............. *A01N 25/00* (2013.01); *A01N 43/40* (2013.01); *A01N 33/12* (2013.01)

(58) Field of Classification Search
CPC .............................. A01N 43/43; A01N 33/12
USPC ................................................. 504/130, 345
See application file for complete search history.

(56) References Cited

U.S. PATENT DOCUMENTS

| | | | |
|---|---|---|---|
| 3,852,340 A | 12/1974 | Reck et al. | |
| 4,534,783 A | 8/1985 | Beestman | |
| 2005/0170967 A1 | 8/2005 | Parrish et al. | |
| 2006/0183654 A1 | 8/2006 | Small | |
| 2010/0184599 A1* | 7/2010 | Parrish et al. ................ | 504/128 |

FOREIGN PATENT DOCUMENTS

| | | | | |
|---|---|---|---|---|
| DE | 203677 | | 11/1983 | |
| EP | 0183384 A | | 6/1986 | |
| EP | 0274369 A | | 7/1988 | |
| GB | 1056235 | | 1/1967 | |
| GB | 1113735 A | | 6/1968 | |
| GB | 2059412 | * | 8/1980 | ............. A01N 33/04 |
| GB | 2059412 A | | 8/1980 | |
| JP | 51-106728 | | 3/1975 | |
| WO | PCT/US2008/002488 | | 2/2008 | |

OTHER PUBLICATIONS

Ranz et al. (Screening and optimization of the derivativation of polar herbicides with trimethylanilinium hydroxide for GC-MS analysis, J. Biochem. Biophys. Methods 69 (2006), p. 3-14).*
Rompa et al. (Derivatisation in gas chromatographic determination of acidic herbicides in aqueous environmental samples, Anal Bioanal Chem (2003), Springer-Verlag, 377, p. 590-599).*
Rompa et al. (Derivativation of Acidic Herbicides with selected tetraalykyl ammonium and trimethyl sulfonium hydroxides for their GC Analysis, Analytical Letters, vol. 37, No. 15, 2004, p. 3299-3312).*
DiTomasco et al. (Yellow Starthistle Management Guide, California Invasive Plant Council, Sep. 2006, p. 41-49).*
International Search Report for PCT/US2008/002488, Jun. 18, 2008, Dow AgroSciences LLC [Vincent J. Kramer et al.].
U.S. Appl. No. 12/072,439, filed Feb. 26, 2008: "Ionic Liquids Derived from Herbicidal Carboxylic Acids and Certain Trialkylamines or Heteroarylamines" (claiming priority of U.S. Appl. No. 60/903,418).
J. Pernak and I. Goc, "New Ionic Liquids with Organic Anions," Polish J. Chem, 77, 975-984 (2003).
Susan L. Bell, SRI Consulting Report No. 256: "Ionic Liquids," Process Economics Program, Menlo Park, California, Sep. 2004.
Cinzia Chiappe and Daniela Pieraccini, "Ionic Liquids: Solvent Properties and Organic Reactivity," Journal of Physical Organic Chemistry 2005; 18: 275-297.
Patricia L. Short, "Out of the Ivory Tower," Chemical & Engineering News, 2006.
Michael Freemantle, "New Frontiers for Ionic Liquids," Chemical & Engineering News, Jan. 1, 2007, 23-26.
Callis, Judy, Auxin Action, Nature, May 26, 2005, pp. 436-437, vol. 435.
Mithila, J.; Hall, J. Christopher; Johnson, William G.; Kelley, Kevin B.; Riechers, Dean E., Evolution of Resistance to Auxinic Herbicides: Historical Perspectives, Mechanims of Resistance, and Implications for Broadleaf Weed Management in Agronomic Crops, Weed Science, 2011, pp. 445-457, vol. 59(4), Weed Science Society of America.
Guilfoyle, Tom, Sticking with Auxin, Nature, Apr. 5, 2007, pp. 621-622, vol. 446.
Fishel, Frederick M., Plant Growth Regulators, University of Florida, pp. 1-4, PI-102.
A. Ranz; E Lankmayr, Screening and Optimization of the Derivatization of Polar Herbicides with Trimethylanilinium Hydroxide for GC-MS Analysis, Journal of Biochemical and Biophysical Methods, 69 (2006) 3-14.
Martyna Rompa, Ewa Kremer, Bogdan Zygmunt, Derivatisation in Gas Chromatographic Determination of Acidic Herbicides in Aqueous Environmental Samples, Anal Bioanal Chem (2003) 377: 590-599.
Nihal Dharmasiri; Sunethra Dharmasiril Mark Estelle, The F-box Protein TIR1 is an Auxin Receptor, Nature, May 26, 2005; vol. 435, p. 441.
Kepinski, Stefan and Leyser, Ottoline, The Arabidopsis F-box Protein TIR1 is an Auxin Receptor, Nature, May 26, 2005, vol. 435, Ph 446.
G.D. Yadav and Yogeeta B. Jadhav, Synthesis of 2,4-dichlorophenoxyacetic Acid: Novelties of Kinetics of Inverse Phase Transfer Catalysis, Journal of Molecular Catalysis A: Chemical 184 (2002) 151-160.

(Continued)

*Primary Examiner* — Johann R Richter
*Assistant Examiner* — Danielle Sullivan
(74) *Attorney, Agent, or Firm* — Michael J. Terapane

(57) ABSTRACT

Compounds formed by combining a carboxylic acid herbicide with N—(($C_1$-$C_{16}$)alkyl or arylalkyl) tri(($C_1$-$C_{16}$)alkyl) ammonium hydroxide have herbicidal activity on an acid equivalent basis at least as active as the commercially used carboxylic acid herbicide salts, but are less volatile.

8 Claims, No Drawings

(56) References Cited

OTHER PUBLICATIONS

United States Environmental Protection Agency, Letter to Jon C. Wood dated Dec. 15, 2003 re: Revides Labeling, Citrus Fix Plant Growth Regulator, EPA Registration No. 5481-145. 8 pages.

Sterling, Tracy M. and Hall, Christopher J., Mechanism of Action of Natural Auxins and Auxinic Herbicides, Herbicide Activity: Toxicology, Biochemistry, and Molecular Biology, IOS Press, 1997, pp. 111-112.

Szabo, Steve S. The Hydrolysis of 2,4-D Esters by Bean and Corn Plants, Weeds, vol. 11, No. 4 (Oct. 1963), pp. 292-294.

Morre, D. James and Rogers, B.J., The Fate of Long Chain Esters of 2,4-D in Plants, Weeds, vol. 8, No. 3 (Jul. 1960), pp. 436-447.

A.S. Crafts, Evidence of Hydrolysis of Esters of 2,4-D during Absorption by Plants, Weeds, vol. 8, No. 1 (Jan. 1960), pp. 19-25.

Rompa, et al. Derivatization of Acidic Herbicides with Selected Tetraalkyl Ammonium and Trimethyl Sulfonium Hyrdoxides for Their GC Analysis, Analytical Letters, vol. 37, No. 15, 2004, pp. 3299-3212.

* cited by examiner

COMPOUNDS DERIVED FROM HERBICIDAL CARBOXYLIC ACIDS AND TETRAALKYLAMMONIUM OR (ARYLALKYL) TRIALKYLAMMONIUM HYDROXIDES

This application claims the benefit of U.S. Provisional Application Ser. No. 60/903,417 filed on Feb. 26, 2007. The present invention relates to compounds (liquids or solids) formed by combining a carboxylic acid herbicide with a tetraalkylammonium or an (arylalkyl)trialkylammonium hydroxide.

Acid herbicides such as 2,4-dichlorophenoxyacetic acid (2,4-D) have long been used to control unwanted vegetation. 2,4-D is normally converted into liquid formulations by conversion to water soluble salts or emulsified esters. The ester formulations have been found to be more effective than the salts on an acid equivalent basis in the control of noxious vegetation but have the unwanted characteristic of migrating to adjacent desirable vegetation because of the volatility thereof, resulting in unacceptable damage to sensitive plants.

Efforts to solve the volatility problem, including preparation of water soluble salts such as the dimethylamine salt of 2,4-D, have not been totally satisfactory because, upon volatilization of the amine, the herbicide reverts back to its initial acid form, which, in itself under certain unfavorable conditions, has sufficient volatility to cause damage to sensitive crops.

2,4-D ester or 2,4-D dimethylamine formulations applied during the warm summer months can lead to vapor drift from the evaporation of the herbicide from sprayed surfaces and subsequent damage to highly susceptible crops such as tomatoes, cotton, soybeans, sunflowers and grapes. This may occur within hours after the herbicide application.

Thus it would be desirable to have an herbicidal carboxylic acid derivative that is at least as active as the commercially used carboxylic acid herbicide salts, but which is less volatile so that its use would not damage nearby sensitive crops.

SUMMARY OF THE INVENTION

It has now been found that compounds formed by combining a carboxylic acid herbicide with either a tetraalkylammonium or an (arylalkyl)trialkylammonium hydroxide have herbicidal activity on an acid equivalent basis at least comparable to the commercially used carboxylic acid herbicide salts, but with reduced volatility. Furthermore, the compounds can be more conveniently formulated as aqueous concentrates or emulsified liquids. The present invention concerns herbicidal compounds comprising the reaction product of an herbicidal carboxylic acid and an N—(($C_1$-$C_{16}$)alkyl or arylalkyl) tri (($C_1$-$C_{16}$)alkyl)ammonium hydroxide, where the alkyl groups can be the same or different. The invention includes herbicidal compositions comprising an herbicidally effective amount of such compounds in admixture with an agriculturally acceptable adjuvant or carrier. The invention also includes a method of use of the compounds and their compositions of the present invention to kill or control undesirable vegetation by application of an herbicidal amount of the compound to the vegetation or to the locus of the vegetation as well as to the soil prior to emergence of the vegetation.

DETAILED DESCRIPTION OF THE INVENTION

Unless specifically limited otherwise, the term "alkyl", as well as derivative terms such as "arylalkyl", as used herein, include within their scope straight chain, branched chain and cyclic moieties. Unless specifically stated otherwise, each may be unsubstituted or substituted with one or more substituents selected from but not limited to halogen, hydroxy, alkoxy or alkylthio, provided that the substituents are sterically compatible and the rules of chemical bonding and strain energy are satisfied. The term "aryl" refers to a phenyl, indanyl or naphthyl group. The aryl group may be unsubstituted or substituted with one or more substituents selected from halogen, hydroxy, $C_1$-$C_6$ alkyl or $C_1$-$C_6$ alkoxy, provided that the substituents are sterically compatible and the rules of chemical bonding and strain energy are satisfied. The term "arylalkyl" refers to $C_1$-$C_4$ alkyl groups substituted with an aryl group.

Herbicidal carboxylic acids mean those herbicides containing a carboxylic acid group and includes benzoic acid herbicides such as chloramben, dicamba, 2,3,6-TBA and tricamba; organophosphorus herbicides such as glufosinate and glyphosate; pyrimidinyloxybenzoic acid herbicides such as bispyribac and pyriminobac; phthalic acid herbicides such as chlorthal; pyridine carboxylic acid herbicides such as aminopyralid, clopyralid, fluoroxypyr, picloram and triclopyr; quinolinecarboxylic acid herbicides such as quinclorac and quinmerac; phenoxyacetic herbicides such as 4-CPA, 2,4-D, 3,4-DA and MCPA; phenoxybutyric herbicides such as 4-CPB, 2,4-DB, 3,4-DB and MCPB; phenoxypropionic herbicides such as cloprop, 4-CPP, dichlorprop, 3,4-DP, fenoprop, mecopropand mecoprop-P; and aryloxyphenoxypropionic herbicides such as chlorazifop, clodinafop, clofop, cyhalofop, diclofop, fenoxaprop, fluazifop, haloxyfop, isoxapyrifop, metamifop, propaquizafop, quizalofop and trifop. Preferred herbicidal carboxylic acids are 2,4-D, triclopyr, aminopyralid, clopyralid, fluoroxypyr, picloram, cyhalofop, fluazifop, haloxyfop, clodinafop, fenoxaprop, dicamba, glufosinate and glyphosate.

N—(($C_1$-$C_{16}$)Alkyl or arylalkyl) tri(($C_1$-$C_{16}$)alkyl)ammonium hydroxide refers to compounds of the formula

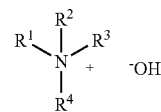

wherein $R^1$, $R^2$ and $R^3$ independently represents ($C_1$-$C_{16}$) alkyl or any two of $R^1$, $R^2$ and $R^3$ represent —$(CH_2)_n$— where n is an integer from 3-5 and $R^4$ represents (($C_1$-$C_{16}$)alkyl or arylalkyl). Preferred N—(($C_1$-$C_{16}$)alkyl or arylalkyl) tri(($C_1$-$C_{16}$)alkyl)ammonium hydroxides are those in which $R^1$, $R^2$, $R^3$ and $R^4$ are the same or where $R^1$, $R^2$ and $R^3$ are $CH_3$ and $R^4$ is ($C_2$-$C_{16}$)alkyl or arylalkyl.

The compounds of the present invention can be conveniently prepared by reaction of the herbicidal carboxylic acid with an appropriate N—(($C_1$-$C_{16}$)alkyl or arylalkyl) tri(($C_1$-$C_{16}$)alkyl)ammonium hydroxide. The herbicidal carboxylic acid is mixed with the N—(($C_1$-$C_{16}$)alkyl or arylalkyl) tri (($C_1$-$C_{16}$)alkyl)ammonium hydroxide in a solvent like methanol followed by removal of the solvent and any water generated or present in the N—(($C_1$-$C_{16}$)alkyl or arylalkyl) tri(($C_1$-$C_{16}$)alkyl)ammonium hydroxide reactant under vacuum.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action.

Application rates of about 1 to about 2,000 g/Ha are generally employed in both postemergence and preemergence applications. The higher rates designated generally give non-selective control of a broad variety of undesirable vegetation. The lower rates typically give selective control and can be employed in the locus of crops.

The compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. The compounds of the present invention can, further, be used in conjunction with glyphosate, glufosinate or 2,4-D on glyphosate-tolerant, glufosinate-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The compounds of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenylsulfonylbenzoic acid amides, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are acetolactate synthase inhibitors in sensitive plants can be treated. Many glyphosate and glufosinate tolerant crops can be treated as well, alone or in combination with these compounds. Some crops (e.g. cotton) have been made tolerant to auxinic herbicides such as 2,4-dichlorophenoxyacetic acid. These compounds may be used to treat such resistant crops or other auxin tolerant crops.

While it is possible to utilize the compounds directly as herbicides, it is preferable to use them in mixtures containing a herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calciumdodecyl-benzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethyl-ammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like.

The compositions may also contain other compatible components, for example, other herbicides, plant growth regulators, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 2 weight percent active ingredient and preferably contain about 0.01 to about 1 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims.

GENERAL PREPARATIVE EXAMPLE

The carboxylic acid herbicide and the N—(($C_1$-$C_{16}$)alkyl or arylalkyl) tri(($C_1$-$C_{16}$)alkyl)ammonium hydroxide are combined in equimolar amounts in methanol at room temperature to give a solution of the ammonium salt of the carboxylic acid. The product is then isolated by evaporative removal of the methanol (and any water present) at room temperature to 50° C. The products may be purified by methods known in the art to provide the compounds of the present invention as liquids or solids. Alternatively, the products of the invention may be prepared in water solvent and used as obtained. Table I below lists the compounds prepared in this manner with their physical state and MP where applicable.

Alternatively, the samples may be prepared by combining equimolar amounts of the carboxylic acid herbicide, an N—(($C_1$-$C_{16}$)alkyl or arylalkyl) tri(($C_1$-$C_{16}$)alkyl)ammonium halide (such as chloride or bromide) and a metal hydroxide (such as sodium or potassium hydroxide) in a solvent such as methanol. The product is then isolated by evaporative removal of the methanol (and any water present) at room temperature to 50° C. and removing the metal halide salt by selective dissolution in water, to provide the compounds of the present invention as liquids or solids.

TABLE I

| Compound | Amine | Acid | Physical State | Melting Range (° C.) |
| --- | --- | --- | --- | --- |
| 1a | tetramethylammonium hydroxide | 2,4-D | solid | 213-216 dec |
| 1b | tetraethylammonium hydroxide | 2,4-D | liquid | 95-105 |
| 1c | tetrapropyl ammonium hydroxide | 2,4-D | liquid | NA |
| 1d | tetrabutyl ammonium hydroxide | 2,4-D | solid | 53-58 |
| 1e | choline hydroxide | 2,4-D | solid | 105-120 |
| 1f | N-benzyltrimethylammonium hydroxide | 2,4-D | solid | 84-86 |
| 1g | N-hexadecyltrimethylammonium hydroxide | 2,4-D | solid | 65-72 |
| 2a | tetramethylammonium hydroxide | triclopyr | solid | >170 dec |
| 2b | tetraethylammonium hydroxide | triclopyr | solid | 79-86 |
| 2c | tetrapropyl ammonium hydroxide | triclopyr | liquid | NA |
| 2d | tetrabutyl ammonium hydroxide | triclopyr | solid | 88-93 |
| 2e | choline hydroxide | triclopyr | solid | >160 dec |
| 2f | N-benzyltrimethylammonium hydroxide | triclopyr | solid | 166-171 dec |
| 2g | N-hexadecyltrimethylammonium hydroxide | triclopyr | solid | 73-77 |
| 3a | tetramethylammonium hydroxide | cyhalofop | solid | 144-155 |
| 3b | tetrabutyl ammonium hydroxide | cyhalofop | liquid | NA |
| 3c | N-benzyltrimethylammonium hydroxide | cyhalofop | solid | 162-166 |
| 3d | N-hexadecyltrimethylammonium hydroxide | cyhalofop | liquid | NA |
| 4a | tetramethylammonium hydroxide | dicamba | solid | 175-181 dec |

Post-Emergence Application Methods for Herbicide Evaluations.

A peat based potting soil, Metro-mix 360, was used as the soil media for this test. Metro-mix is a growing medium consisting of 35 to 45% specially processed Coconut Coir Pith, 10 to 20% horticultural grade vermiculite, 15 to 25% processed Ash Bark, 20 to 30% choice Canadian Sphagnum Peat Moss and proprietary nutrients and other ingredients. Several seeds of each species were planted in 10 cm square pots and top watered twice daily. Plant material was propagated in the greenhouse at a constant temperature of 26 to 28° C. and 50 to 60% relative humidity. Natural light was supplemented with 1000-watt metal halide overhead lamps with an average illumination of 500 $\mu E\ m^{-2}\ s^{-1}$ photosynthetic active radiation (PAR). Day length was 16 hours. Plant material was top-watered prior to treatment and sub-irrigated after treatment. Treatments were applied with a tracksprayer manufactured by Allen Machine Works. The sprayer utilized an 8002E spray nozzle, spray pressure of 262 kPa pressure and speed of 1.5 mph (2.4 km/h) to deliver 187 L/Ha. The nozzle height was 46 cm above the plant canopy. The growth stage of the various weed species ranged from 2 to 4 leaf. Treatments were replicated 3 times. Plants were returned to the greenhouse after treatment and sub-watered throughout the duration of the experiment. Plant material was fertilized twice weekly with Hoagland's fertilizer solution. Percent visual injury assessments were made on a scale of 0 to 100% as compared to the untreated control plants (where 0 is equal to no injury and 100 is equal to complete death of the plant). The results are listed in Table II.

TABLE II

Efficacy data generated in the greenhouse for 2,4-D and triclopyr on broadleaf weeds. Data are from evaluations taken 14 days after application.

| Treatment/Compound Number | Rate (g ae/ha) | Broadleaf Dock *Rumex obtusifolia* | Kochia *Kochia scoparia* |
|---|---|---|---|
| | | % Control | |
| 2,4-D dimethylamine (DMA) | 560 | 77 | 86 |
| 1a | 560 | 77 | 83 |
| 1b | 560 | 79 | 89 |
| 1c | 560 | 73 | 83 |
| 1e | 560 | 68 | 86 |
| Triclopyr triethylamine (TEA) | 560 | 81 | 91 |
| 2a | 560 | 85 | 79 |
| 2b | 560 | 79 | 88 |
| 2c | 560 | 79 | 95 |

Method for Evaluating the Volatility of Herbicide Standards and the Compounds Derived from Combining a Carboxylic Acid Herbicide with Either a Tetraalkylammonium or an (Arylalkyl)Trialkylammonium Hydroxide.

Four pots of wheat (*Triticum aestivum* L.) grown in 4 inch square pots were sprayed at 11200 g ae/ha with each of the different forms of 2,4-D. Treatments were applied with a tracksprayer manufactured by Allen Machine Works. The sprayer utilized an 8002E spray nozzle, spray pressure of 262 kPa pressure and speed of 1.5 mph (2.4 km/h) to deliver 187 L/Ha. The nozzle height was 46 cm above the plant canopy. The growth stage of the wheat was 1 to 2 leaf. The wheat plants were allowed to thoroughly dry to ensure that none of the spray solution was present when they were moved into a clean pot flat. A known sensitive species, grapes (*Vitis labrusca* L.) were placed at the opposite end of the flat. All of the pots were covered with a humidome with small ½ inch (1.27 cm) diameter holes cut into the end where the wheat was placed and a small box fan powered with a battery in the other end to pull air across the treated wheat plants and over the top of grapes. Plants were placed into a growth chamber with the temperature set at 40° C. with a 14 hour day and a 10 hour night cycle. A 24 hour exposure period was used after which the sensitive plants were then removed and placed in the greenhouse and evaluated for injury from vapor exposure to the treatments. The results are listed in Table III.

TABLE III

Injury to grapes from vapor exposure for 24 hours to various forms of 2,4-D, Triclopyr and Dicamba. Evaluations were taken 7 days after exposure to the vapors.

| Treatment/Compound Number | % Injury |
|---|---|
| 2,-4-D butoxyethylester (BEE) | 100 |
| 2,-4-D dimethylamine (DMA) | 78 |
| 1b | 0 |
| Triclopyr triethylamine (TEA) | 57 |
| 2b | 6 |
| Dicamba DMA | 70 |
| 4a | 12 |

What is claimed is:

1. An herbicidal compound comprising the reaction product of an herbicidal carboxylic acid selected from 2,4-D, triclopyr, aminopyralid, clopyralid, fluroxypyr, picloram, cyhalofop, fluazifop, haloxyfop, clodinafop, fenoxaprop, dicamba, glufosinate, and glyphosate and a (tetraalkyl) ammonium hydroxide of the formula

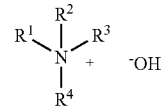

wherein $R^1$, $R^2$ and $R^3$ independently represents $(C_1$-$C_{16})$ alkyl or any two of $R^1$, $R^2$ and $R^3$ may join to form a ring represented by —$(CH_2)_n$— where n is an integer from 3-5 and $R^4$ represents $((C_2$-$C_4)$ alkyl or arylalkyl.

2. An herbicidal compound of claim 1 in which the herbicidal carboxylic acid is 2,4-D, triclopyr, or dicamba.

3. An herbicidal composition comprising an herbicidally effective amount of a compound, as claimed in claim 1, or mixtures thereof, in admixture with an agriculturally acceptable adjuvant or carrier.

4. An herbicidal compound comprising the reaction product of choline hydroxide and 2,4-D, triclopyr, or dicamba.

5. An herbicidal compound of claim 4 in which the herbicidal carboxylic acid is triclopyr.

6. An herbicidal compound of claim 4 in which the herbicidal carboxylic acid is dicamba.

7. An herbicidal composition comprising an herbicidally effective amount of a compound, as claimed in claim 4, or mixtures thereof, in admixture with an agriculturally acceptable adjuvant or carrier.

8. An herbicidal compound of claim 4 in which the herbicidal carboxylic acid is 2,4-D.

* * * * *